United States Patent [19]

Averill et al.

[11] Patent Number: 4,719,908
[45] Date of Patent: Jan. 19, 1988

[54] METHOD AND APPARATUS FOR IMPLANTING A PROSTHETIC DEVICE

[75] Inventors: Robert G. Averill, Ringwood; Christopher G. Sidebotham, Bergenfield, both of N.J.

[73] Assignee: Osteonics Corp., Allendale, N.J.

[21] Appl. No.: 897,139

[22] Filed: Aug. 15, 1986

[51] Int. Cl.[4] .................................................. A61E 5/04
[52] U.S. Cl. ............................ 128/92 VW; 128/92 VY
[58] Field of Search .......... 128/92 VY, 92 VW, 92 V, 128/92 VV

[56] References Cited

U.S. PATENT DOCUMENTS 3,852,830  12/1974  Marmor .................. 128/92 VW
4,344,192  8/1982  Imbert .................... 128/92 VY Primary Examiner—C. Fred Rosenbaum
Assistant Examiner—C. W. Shedd
Attorney, Agent, or Firm—Samuelson & Jacob

[57] ABSTRACT

Method and apparatus for preparing the bone at a joint for the implant of a component part of a prosthetic device include a contouring guide placed on the bone at a predetermined site and having a guide rail for delineating a path of travel to which a contouring cutter is confined while translated along the contouring guide for removing bone along a surface of predetermined area and contour to establish an accurately defined seating area for the component part with minimal intrusion into the joint.

31 Claims, 9 Drawing Figures

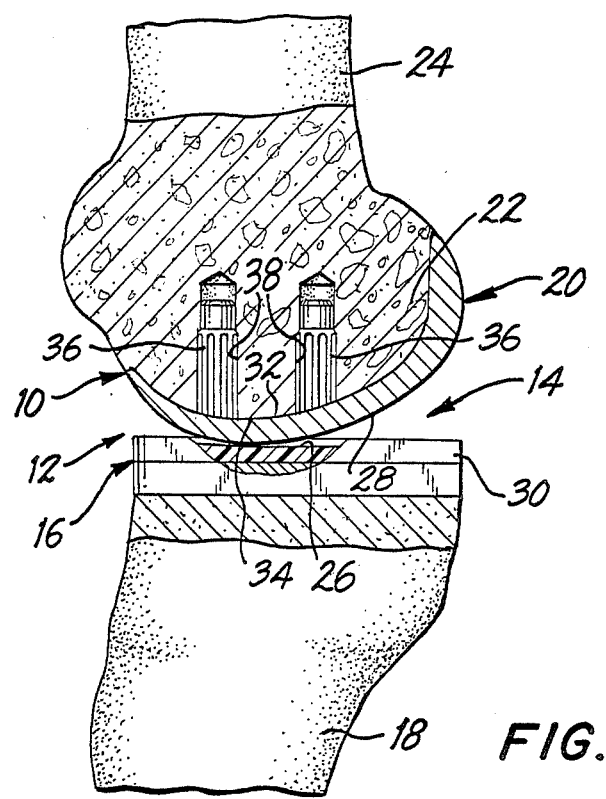
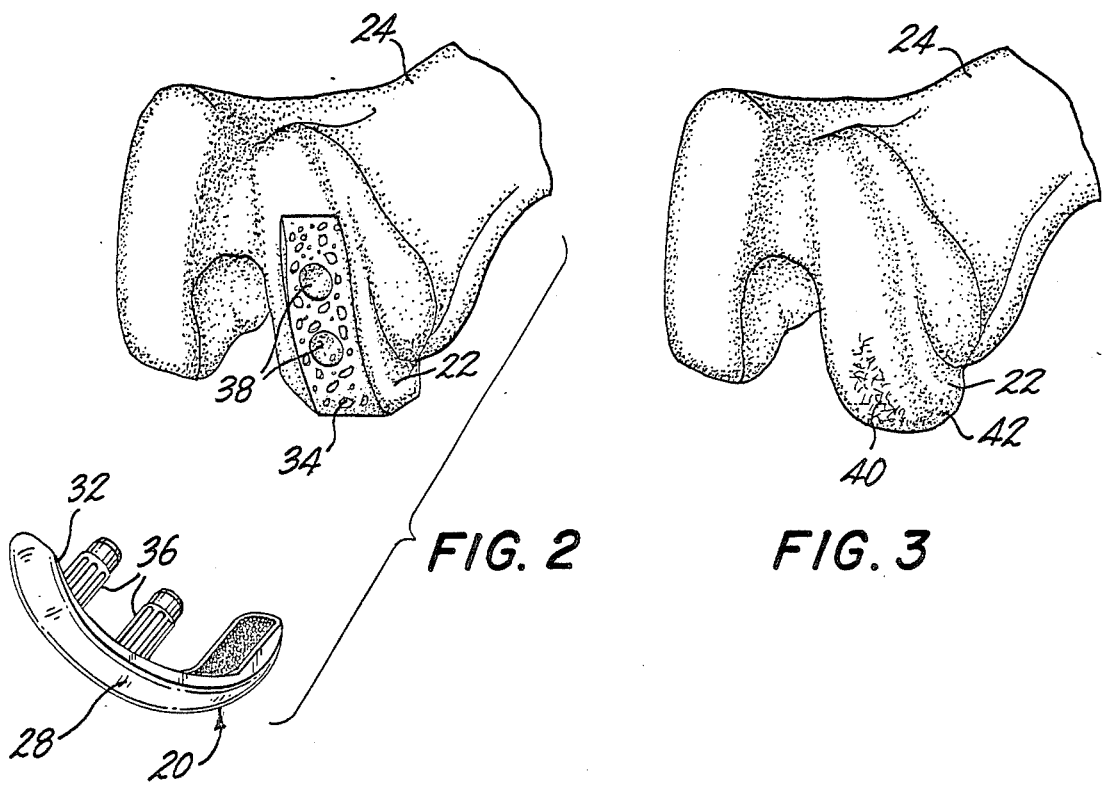
FIG. 1
FIG. 2
FIG. 3

METHOD AND APPARATUS FOR IMPLANTING A PROSTHETIC DEVICE

The present invention relates generally to the implant of prosthetic devices at various joints in the body and pertains, more specifically, to method and apparatus for preparing the bone at the joint for receiving part or parts of the protsthetic device to be implanted.

The use of prosthetic devices to replace damaged joints, or portions of such joints, in the body is becoming more and more widespread as medical and technological advances are joined to provide improved materials and configurations for prosthetic devices and innovative procedures for implanting these devices. The basic objective of such devices and procedures, of course, is to provide a repaired joint of maximum effectiveness, with a minimal intrusion into the body of the recipient of the device. Component parts of the prosthetic device are utilized to replace portions of a natural joint which have become damaged, either through injury or disease, and it is usually necessary to remove portions of the natural joint beyond merely the damaged portions in order to enable stable and secure affixation of the component parts to the natural bone. In addition, access to damaged joints is limited and the necessity for reaching the areas to be worked upon can affect the extent of intrusion required to complete an effective implant.

Among the objects of the present invention in providing an improved method and apparatus by which a prosthetic device may be implanted at the joint of a body are the following: Removal of only a minimal amount of the natural bone at the joint, consistent with enabling stable and secure affixation of each component part of the prosthetic device; the attainment of accuracy in the delineation of the area and contour of the prepared surfaces of the bone which will receive a component part; the ability to attain such accuracy within the confines of the limited access available at the joint, with minimal disturbance of surrounding tissue in the vicinity of the joint; the use of a minimum number of components and steps of limited complexity in carrying out the procedure; and the ability to use currently available instruments in connection with the components of the present apparatus and current techniques in connection with the steps of the present method for compatibility and widespread acceptance among practitioners.

The above objects, as well as still further objects and advantages, are attained by the present invention which may be described briefly as apparatus and method for preparing a seating surface of prescribed area and contour on the bone of a joint at which a prosthetic device is to be implanted, the bone having been provided with at least a partially prepared site for locating and seating a component part of the prosthetic joint at the seating surface. The apparatus includes a contouring guide having opposite ends and an upper locator surface extending longitudinally along the contouring guide between the opposite ends, the upper locator surface having a profile contour essentially matching the contour of the prescribed area of the seating surface, holding means integral with the contouring guide for holding the contouring guide on the bone at the site with the upper locator surface placed at a predetermined location relative to the bone above the bone and along the bone, and a cutter having a cutting surface and a bearing surface adjacent to the cutting surface, the bearing surface being located relative to the cutting surface and the upper locator surface of the contouring guide such that upon engagement of the bearing surface with the upper locator surface the cutting surface will enter the bone up to a limited depth of cut determined by the predetermined location of the upper locator surface above the bone and upon longitudinal translation of the bearing surface along the contouring guide, the cutting surface will cut the bone along a limited length of cut determined by the length of the upper locator surface along the bone to prepare the seating surface of prescribed area and contour. The method includes positioning a contouring guide on the bone at the site so as to locate and hold the contouring guide in place over a portion of the bone, with the contouring guide delineating a longitudinal path of travel, engaging a cutter with the contouring guide such that cutting portions of the cutter enter the bone while bearing portions of the cutter engage the contouring guide, and translating the cutter longitudinally along the contouring guide such that the cutter is confined to the path of travel delineated by the contouring guide and the seating surface is prepared with the prescribed area and contour.

The invention will be understood more fully, while still further objects and advantages will become apparent, in the following detailed description of a preferred embodiment thereof illustrated in the accompanying drawing, in which:

FIG. 1 is a pictorial view, partially cross-sectioned, of a body joint in the form of a knee joint within which a prosthetic device has been implanted;

FIG. 2 is a fragmentary perspective view showing the femoral component of the prosthetic device about to be affixed to a femoral condyle;

FIG. 3 is a fragmentary perspective view showing the femoral condyles prior to one condyle being prepared for the implant of a prosthetic device;

Figure 4:
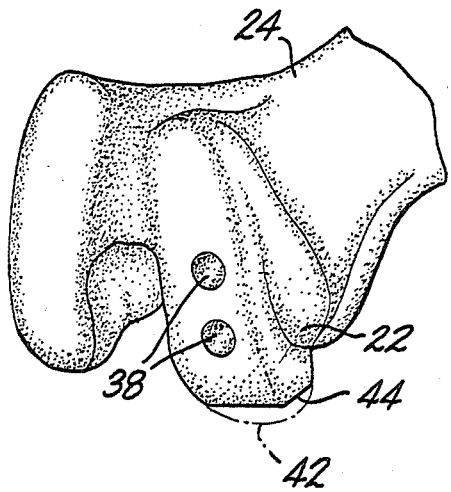
FIG. 4 is a fragmentary perspective view showing the femoral condyles with the medial side compartment partially prepared to receive the femoral component.

Referring now to the drawing, and especially to FIG. 1 thereof, a prosthetic device is illustrated in the form of a unicompartmental knee prosthesis 10 implanted in the medial side compartment 12 of a knee joint 14. Knee prosthesis 10 includes a tibial component 16 affixed to the tibia 18 and a femoral component 20 affixed to the femoral condyle 22 of the medial side compartment 12 of the femur 24. The tibial component 16 provides an articular surface 26 upon which the outer surface 28 of the femoral component 20 moves during articulation of the knee joint 14.

Tibial component 16 includes a tibial pad 30 constructed of a synthetic resin material, such as a high-density polyethylene, which provides the articular surface 26 with the appropriate lubricity characteristics for proper functioning of the prosthesis 10. Femoral component 20 preferably is constructed of a metallic material compatible with its use within the body. The arcuate outer surface 28 replaces the damaged natural bone of the femoral condyle 22 and follows, as closely as is practicable, the contour of the replaced bone. It is desirable to fit the femoral component 20 accurately to the condyle 22 so that the inner surface 32 of the femoral component 20 is contiguous with a seating surface 34 on the condyle 22. In this manner, only minimal bone is removed, enabling the femoral component 20 to be seated upon a superior foundation provided by the relatively dense, stronger bone available nearer the outer surface of condyle 22, and by the geometric contour of the seating surface 34. In addition, the intimate contact attained between the inner surface 32 of the femoral component 20 and the seating surface 34 enhances fixation, either with or without the use of adhesive. A pair of fixation posts 36 on the femoral component 20 project from the inner surface 32 and are inserted into complementary holes 38 in the condyle 22 to accurately locate the femoral component 20 on the condyle 22 and hold the femoral component 20 in that location.

In FIG. 2, the femoral component 20 is about to be implanted on the condyle 22. The condyle 22 has been prepared in accordance with the present invention as will be described more fully below, so that the seating surface 34 is ready to receive the inner surface 32 of the femoral component 20 in the desired contiguous mating relationship.

Turning now to FIG. 3, the femur 24 is shown prior to the preparation of femoral condyle 22 for the implant of femoral component 20. Damaged bone 40 of condyle 22 is to be removed and the femoral component 20 is to be implanted to replace the function of the damaged bone 40 in the knee joint 14.

In FIG. 4, condyle 22 has been prepared partially by drilling holes 38 and sawing off a portion 42 of the condyle 22 to establish a flat surface 44. Both the drilling and the sawing steps are conventional in current implant procedures and fixtures are available for assuring that the holes 38 and the flat surface 44 are located accurately on the condyle 22.

Figure 5:
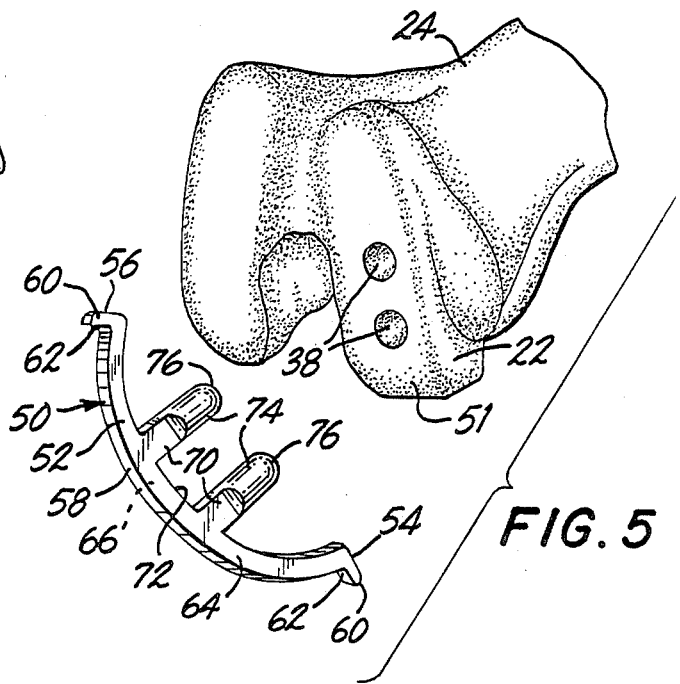
FIG. 5 is a fragmentary perspective view showing a contouring guide constructed in accordance with the invention about to be installed on the partially prepared condyle.

Referring now to FIG. 5, a contouring guide constructed in accordance with the invention is shown at 50 and is about to be installed at the partially prepared site 51 on condyle 22 for assisting in the further preparation of the condyle 22 to receive femoral component 20. Contouring guide 50 includes a guide rail 52 having opposite ends 54 and 56 and an upper locator surface 58 extending longitudinally along guide rail 52 between the opposite ends 54 and 56. A stop 60 is placed at each end 54 and 56 and includes a stop shoulder 62 projecting altitudinally upwardly beyond the upper locator surface 58. Guide rail 52 also includes a lateral width between side locator surfaces 64 and 66 at each side of the guide rail 52, the side locator surfaces 64 and 66 extending altitudinally downwardly from the upper locator surface 58. Preferably, the side locator surfaces 64 and 66 extend in planes parallel to one another and generally perpendicular to the upper locator surface 58.

Contouring guide 50 is to be located and held at site 51 by holding means, here shown in the form of a pair of posts 70 integral with guide rail 52 and projecting altitudnally downwardly from a lower surface 72 of guide rail 52. Each post 70 preferably is aligned altitudinally with guide rail 52 and includes a generally cylindrical pin portion 74 terminating at a rounded terminal end 76. Pin portions 74 are generally parallel to one another, are spaced apart a distance equal to the spacing between holes 38 in condyle 22 and have a diameter slightly smaller than the diameter of holes 38 so that the relative dimensions of the pin portion 74 of each post 70 and a corresponding hole 38 enables insertion of posts 70 into holes 38 for locating the guide rail 52 relative to holes 38 and holding the contouring guide 50 in place on condyle 22, the insertion being facilitated by the rounded configuration of terminal ends 76. The fit between the pin portions 74 and the corresponding holes 38 assures accurate location of the guide rail 52 and stable holding of the contouring guide 50 in place at site 51.

Figure 6:
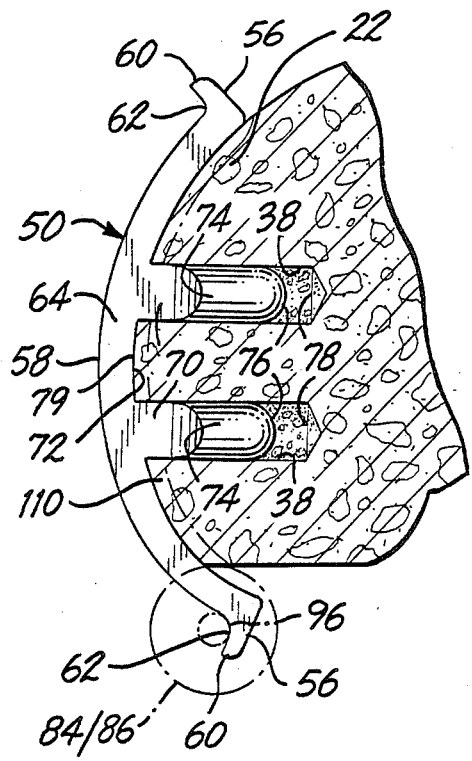
FIG. 6 is an enlarged cross-sectional view showing the contouring guide installed on the partially prepared condyle.

In FIG. 6, the contouring guide 50 is shown installed on condyle 22. The contouring guide 50 has been urged toward the condyle 22, as by light tapping, until the lower surface 72 is seated against the subchondral bone of the condyle 22. Note that holes 38 are deep enough so that the terminal ends 76 of posts 70 are spaced away from the bottom 78 of each hole 38. At the same time, the pin portions 74 are recessed below the outer surface 79 of condyle 22. The upper locator surface 58 is profiled to correspond to the contour of the inner surface 32 of femoral component 20, for purposes which now will be described.

Figure 7:
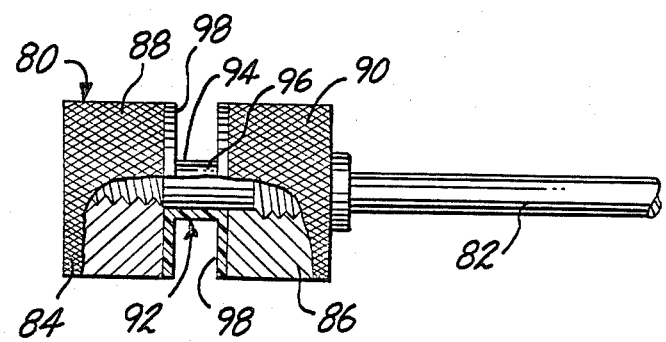
FIG. 7 is an elevational view, partially sectioned, of a contouring cutter constructed in accordance with the invention.

Turning now to FIG. 7, a contouring cutter constructed in accordance with the invention is shown in the form of a burr assembly 80 having a shaft 82 upon which there are mounted cutters 84 and 86 having contoured cutting surfaces, here shown as generally cylindrical cutting surfaces 88 and 90, respectively. The cutters 84 and 86 are threadedly engaged with shaft 82 so that burr assembly 80 rotates as a unit. Cutters 84 and 86 are spaced apart axially to establish an annular groove 92 between the cutters, and a bushing 94 is placed in the groove 92 to provide a cylindrical bearing surface 96 having a diameter smaller than the diameter of cutting surfaces 88 and 90 and radial bearing surfaces 98 along groove 92. Preferably, bushing 94 is constructed of a synthetic resin material having the desired lubricity.

Figure 8:
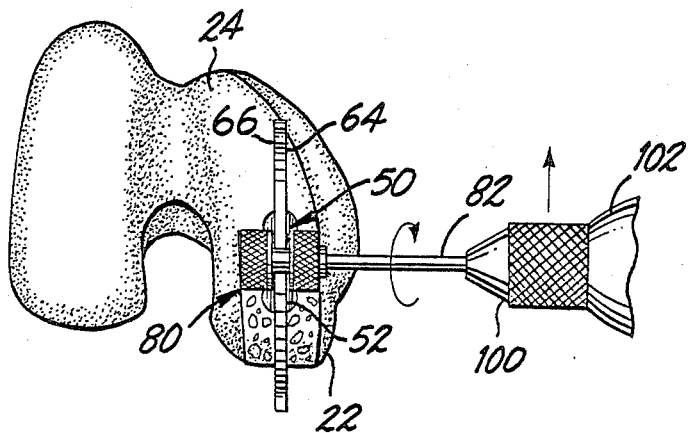
FIG. 8 is a pictorial view showing the contouring cutter engaged with the installed contouring guide during performance of the method of the invention.

As seen in FIG. 8, burr assembly 80 is affixed to a chuck 100 of a power-operated tool 102 for rotation of the burr assembly 80 (preferably at a relatively low speed) and is slipped over guide rail 52 of the installed contouring guide 50. Referring to FIG. 6, as well as to FIG. 8, the relative dimensions of the diameters of the cutters 84 and 86 and the cylindrical bearing surface 96, and the distance between upper locator surface 58 and lower surface 72 of guide rail 52 all are such that upon altitudinal movement of the burr assembly 80 to engage the cylindrical bearing surface 96 with the upper locator surface 58, the cutters 84 and 86 will cut into the bone of the condyle 22 up to a depth determined by the predetermined location of the upper locator surface 58 above the surface 79 of the subchondral bone. Upon longitudinal translation of the burr assembly 80 along the guide rail 52, the cutters 84 and 86 will remove bone along the path of travel of the burr assembly. The path of travel is delineated accurately by the engagement of the cylindrical bearing surface 96 with upper locator surface 58 and the engagement of radial bearing surfaces 98 with the side locator surfaces 64 and 66 of guide rail 52, the radial bearing surfaces 98 being spaced apart axially to receive the guide rail 52 in appropriate complementary bearing relationship. In this manner, the contouring cutter is confined to movement along the path of travel delineated by the contouring guide 50. The stops 60 define the end limits of travel of the burr assembly 80 along the guide rail 52 by providing stop shoulders 62 against which cylindrical bearing surface 96 is abutted when the burr assembly 80 reaches the limits of longitudinal translation.

Once the burr assembly 80 has traversed the length of guide rail 52, a layer of bone will be removed from condyle 22, as indicated at 110 in FIG. 6. The combination of the guide rail 52 and the burr assembly 80 assures that the layer 110 of bone removed is uniform and is relatively thin, generally about 0.050 inch, so that the intrusion into condyle 22 is held to a minimum, consistent with the requirement for the exposure of dense cancellous bone.

Figure 9:
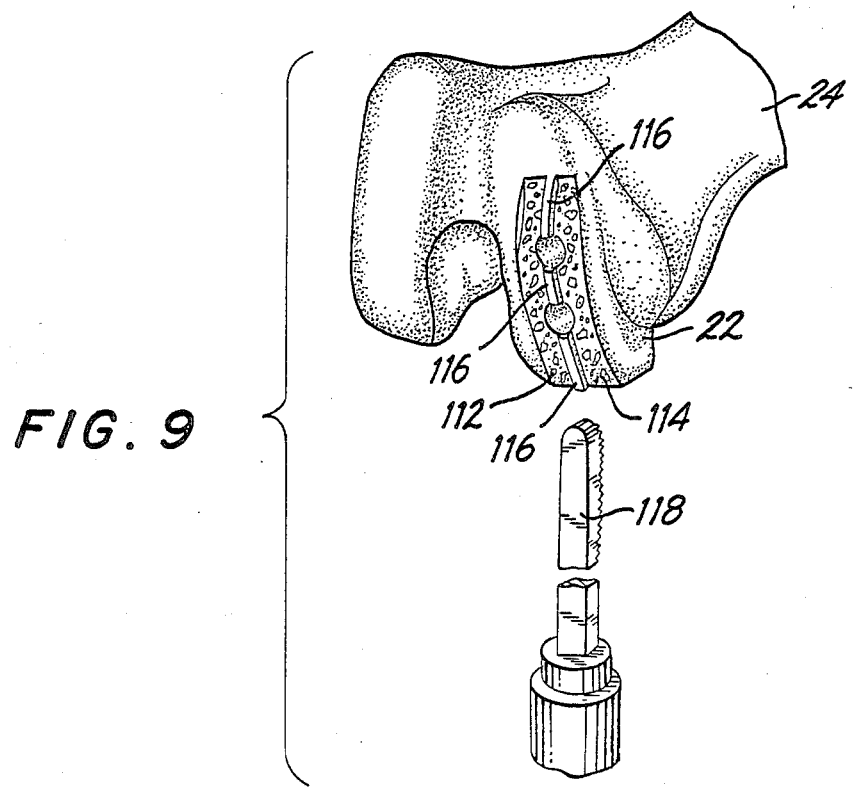
FIG. 9 is a pictorial perspective view showing the condyles subsequent to the procedure of FIG. 8 and prior to a further cutting step.

Turning now to FIG. 9, the contouring guide 50 has been removed, exposing prepared surfaces 112 and 114 and leaving behind thin remnants 116 of subchondral bone which had been masked by the contouring guide 50 during the aforementioned cutting step. The remnants 116 then are removed with a removal tool, here shown in the form of a file 118. Should there be any irregularities in the prepared surfaces 112 and 114, the contouring guide 50 may be installed in condyle 22 once again and another pass of the burr assembly 80 may be completed to remove another thin layer of subchondral bone, the spacing between the terminal ends 76 of posts 70 and bottoms 78 of holes 38 enabling reinstallation of the contouring guide 50 subsequent to removal of layer 110 and remnants 116. The procedure may be repeated until the prepared surfaces 112 and 114 are uniform, exposing the desired bleeding cancellous bone over the prescribed area and contour which constitutes the completed seating surface 34, as illustrated in FIG. 2.

In the illustrated embodiment, the contouring guide 50 is located centrally along the area within which seating surface 34 is to be prepared, and the annular groove 92 of the contouring cutter is centered axially between cutters 84 and 86. Such an arrangement is preferred in that a certain balance is achieved, which balance enhances control of the contouring cutter and eases the conduct of the procedure. However, other arrangements may be chosen for meeting the requirements of particular body joints and corresponding prosthetic devices. While the illustrated embodiment is shown used in connection with a knee joint, it is to be understood that the apparatus and procedure of the invention may be employed in connection with the implant of prosthetic devices in joints other than knee joints.

The above described apparatus and procedure enables the implant of a femoral component 20 while requiring the removal of only a minimal amount of bone from the condyle 22, thereby reducing to a minimum intrusion into the knee joint 14. The preparation of the required accurate seating surface 34 is accomplished with ease, the accuracy of the area and the contour of the seating surface 34 being assured by the close control of the cutting step attained as a result of the configuration of the contouring guide 50 and the mating burr assembly 80. The ability to obtain a controlled curved contour matching the curved contour of the inner surface 32 of femoral component 20 as opposed to freehand cutting or cutting away larger amounts of bone to establish flat mating surfaces, as has been done in the past, renders the present procedure highly advantageous. At the same time, the procedure requires only a relatively compact apparatus, compatible with the limited access available at the knee joint 14, and reducing the intrusion into the knee joint 14 by instruments necessary for the procedure.

While the term "cutting" has been used herein to describe the mechanism by which bone is removed, and the apparatus includes "cutters", it is to be understood that these terms are meant to include removal of bone by any of one of a variety of mechanisms such as, for example, by abrading, sawing, shaving, slicing or the like accomplished by a variety of tools, any one of which is meant to fall within the term "cutter".

It is to be understood that the above detailed description of an embodiment of the invention is provided by way of example only. Various details of design, construction and procedure may be modified without departing from the true spirit and scope of the invention as set forth in the appended claims.

The embodiments of the invention in which an exclusive property or privilege is claimed are defined as follows:

1. Apparatus for preparing a seating surface of prescribed area and contour on the bone of a joint at which a prosthetic device is to be implanted, the bone having been provided with at least a partially prepared site for locating and seating a component part of the prosthetic joint at the seating surface, said apparatus comprising:
   a contouring guide having opposite ends and an upper locator surface extending longitudinally along the contouring guide between the opposite ends;
   the upper locator surface having a profile contour essentially matching the contour of the prescribed area of the seating surface;
   holding means integral with the contouring guide for holding the contouring guide on the bone at the site with the upper locator surface placed at a predetermined location relative to the bone above the bone and along the bone; and
   a cutter having a cutting surface and a bearing surface adjacent to the cutting surface, the bearing surface being located relative to the cutting surface and the upper locator surface of the contouring guide such that upon engagement of the bearing surface with the upper locator surface the cutting surface will enter the bone up to a limited depth of cut determined by the predetermined location of the upper locator surface above the bone and upon longitudinal translation of the bearing surface along the contouring guide, the cutting surface will cut the bone along a limited length of cut determined by the length of the upper locator surface along the bone to prepare the seating surface of prescribed area and contour.

2. The invention of claim 1 wherein the contouring guide includes a rail.

3. The invention of claim 2 wherein the rail includes a stop at each end thereof for limiting the extent of said longitudinal translation of the bearing surface along the rail.

4. The invention of claim 2 wherein:
   the rail includes a side locator surface extending altitudinally relative to the upper locator surface; and the cutter includes a further bearing surface for engagement with the side locator surface to locate the cutter laterally relative to the rail during said longitudinal translation.

5. The invention of claim 2 wherein:
the rail includes opposite side locator surfaces extending altitudinally relative to the upper locating surface; and
the cutter includes further bearing surfaces for engagement with the side locator surfaces to confine movement of the cutter to a prescribed longitudinal path along the rail during said longitudinal translation.

6. The invention of claim 2 wherein the site includes at least one hole in the bone and the holding means includes at least one post projecting in a direction away from the upper locator surface, the relative dimensions of the post and the hole in the bone being such that the post is receivable within the hole to hold the contouring guide on the bone at the site.

7. The invention of claim 6 wherein the post projects altitudinally downwardly and is aligned altitudinally with the rail.

8. The invention of claim 6 wherein the bone is provided with at least one further hole spaced from the one said hole and the invention includes at least one further post integral with the rail and projecting in a direction away from the upper locator surface, the further post being spaced from the one said post to correspond to the spacing between said holes such that each post is receivable within a corresponding hole to locate and hold the rail on the bone.

9. The invention of claim 2 wherein the cutting surface is generally cylindrical, extends axially between opposite ends, and is rotatable about an axis of rotation extending between the opposite ends, and the bearing surface includes a cylindrical bearing portion coaxial with the cutting surface and having a diameter smaller than the diameter of the cutting surface.

10. The invention of claim 9 wherein the cutter includes an annular groove juxtaposed with the cutting surface, and the bearing surface is located in the annular groove.

11. The invention of claim 10 wherein:
the rail includes opposite side locator surfaces extending altitudinally relative to the upper locating surface, and has a lateral width between the opposite side locator surfaces;
the annular groove is located intermediate the opposite ends of the cutting surface and has an axial width complementary to the lateral width of the rail between the opposite side locator surfaces; and
the bearing surface includes radial portions in the groove for engaging the side locator surfaces to confine movement of the cutter to a prescribed longitudinal path along the rail during said longitudinal translation.

12. The invention of claim 11 wherein the rail includes a stop at each end thereof for limiting the extent of said longitudinal translation of the bearing surface along the rail.

13. The invention of claim 12 wherein the site includes at least one hole in the bone and the holding means includes at least one post projecting in a direction away from the upper locator surface, the relative dimensions of the post and the hole in the bone being such that the post is receivable within the hole to hold the contouring guide on the bone at the site.

14. The invention of claim 13 wherein the post projects altitudinally downwardly and is aligned altitudinally with the rail.

15. The invention of claim 13 wherein the bone is provided with at least one further hole spaced from the one said hole and the invention includes at least one further post integral with the rail and projecting in a direction away from the upper locator surface, the further post being spaced from the one said post to correspond to the spacing between said holes such that each post is receivable within a corresponding hole to locate and hold the rail on the bone.

16. In an apparatus for preparing a seating surface of prescribed area and contour on the bone of a joint at which a prosthetic device is to be implanted, the bone having been provided with at least a partially prapared site for locating and seating a component part of the prosthetic joint at the seating surface, guide means for guiding a cutter to cut the bone and establish said seating surface, the cutter including a cutting surface and a bearing surface adjacent to the cutting surface, said guide means comprising:
a contouring guide having opposite ends and an upper loctor surface extending longitudinally along the contouring guide between the opposite ends; the upper locator surface having a profile contour essentially matching the contour of the prescribed area of the seating surface; and
holding means integral with the contouring guide for holding the contouring guide on the bone with the upper locator surface placed at a predetermined location relative to the bone above the bone and along the bone such that upon engagement of the bearing surface with the upper locator surface the cutting surface will enter the bone up to a limited depth of cut determined by the predetermined location of the upper locator surface above the bone, and upon longitudinal translation of the bearing surface along the contouring guide, the cutting surface will cut the bone along a limited length of cut determined by the length of the upper locator surface along the bone to prepare the seating surface of prescribed area and contour.

17. The invention of claim 16 wherein the contouring guide includes a rail.

18. The invention of claim 17 wherein the rail includes a stop at each end thereof for limiting the extent of said longitudinal translation of the bearing surface along the rail.

19. The invention of claim 17 wherein the rail includes a side locator surface extending altitudinally relative to the upper locator surface.

20. The invention of claim 17 wherein the rail includes opposite side locator surfaces extending altitudinally relative to the upper locating surface.

21. The invention of claim 17 wherein the site includes at least one hole in the bone and the holding means includes at least one post projecting in a direction away from the upper locator surface, the relative dimensions of the post and the hole in the bone being such that the post is receivable within the hole to hold the contouring guide on the bone at the site.

22. The invention of claim 21 wherein the post projects altitudinally downwardly and is aligned altitudinally with the rail.

23. The invention of claim 21 wherein the bone is provided with at least one further hole spaced from the one said hole and the invention includes at least one further post integral with the rail and projecting in a direction away from the upper locator surface, the further post being spaced from the one said post to correspond to the spacing between said holes such that each post is receivable within a corresponding hole to locate and hold the rail on the bone.

24. In an apparatus for preparing a seating surface of prescribed area and contour on the bone of a joint at which a prosthetic device is to be implanted, the bone having been provided with at least a partially prepared site for locating and seating a component part of the prosthetic joint at the seating surface, cutting means for cutting the bone to establish said seating surface, the cutting means being guided by a contouring guide having opposite ends and an upper locator surface extending longitudinally along the contouring guide between the opposite ends, the upper locator surface having a profile contour essentially matching the contour of the prescribed area of the seating surface, and holding means integral with the contouring guide for holding the contouring guide on the bone with the upper locator surface placed at a predetermined location relative to the bone above the bone and along the bone, said cutting means comprising:

a cutter having a cutting surface and a bearing surface adjacent to the cutting surface, the bearing surface being located relative to the cutting surface and the upper locator surface of the contouring guide such that upon engagement of the bearing surface with the upper locator surface the cutting surface will enter the bone up to a limited depth of cut determined by the predetermined location of the upper locator surface above the bone and upon longitudinal translation of the bearing surface along the contouring guide, the cutting surface will cut the bone along a limited length of cut determined by the length of the upper locator surface along the bone to prepare the seating surface of prescribed area and contour.

25. The invention of claim 24 wherein the cutting surface is generally cylindrical, extends axially between opposite ends, and is rotatable about an axis of rotation extending between the opposite ends, and the bearing surface includes a cylindrical bearing portion coaxial with the cutting surface and having a diameter smaller than the diameter of the cutting surface.

26. The invention of claim 25 wherein the cutter includes an annular groove juxtaposed with the cutting surface, and the bearing surface is located in the annular groove.

27. The invention of claim 26 wherein:

the contouring guide includes a rail having opposite side locator surfaces extending altitudinally relative to the upper locating surface, and a lateral width between the opposite side locator surfaces;

the annular groove is located intermediate the opposite ends of the cutting surface and has an axial width complementary to the lateral width of the rail between the opposite side locator surfaces; and the bearing surface includes radial portions in the groove for engaging the side locator surfaces to confine movement of the cutter to a prescribed longitudinal path along the rail during said longitudinal translation.

28. The method of preparing a seating surface of prescribed area and contour on the bone of a joint at which a prosthetic device is to be implanted, the bone having been provided with at least a partially prepared site for locating and seating a component part of the prosthetic joint at the seating surface, said method comprising the steps of:

positioning a contouring guide on the bone at said site so as to locate and hold the contouring guide in place over a portion of the bone, with the contouring guide delineating a longitudinal path of travel;

engaging cutting means with the contouring guide such that cutting portions of the cutting means enter the bone while bearing portions of the cutting means engage the contouring guide; and translating the cutting means longitudinally along the contouring guide such that the cutting means is confined to the path of travel delineated by the contouring guide and the seating surface is prepared with said prescribed area and contour.

29. The invention of claim 28 wherein the partially prepared site includes at least one hole in the bone and the step of positioning the contouring guide at the site includes inserting an element of the contouring guide into the hole in the bone.

30. The invention of claim 28 wherein the cutting means includes cutting portions located at both sides of the contouring guide and the method includes cutting the bone simultaneously at both sides of the contouring guide as the cutting means is translated along the contouring guide.

31. The invention of claim 30 including the steps of:

removing the contouring guide from the bone subsequent to said translating of the cutting means along the contouring means; and cutting away the bone along the portion of the bone over which the contour guide had been positioned to complete the preparation of the full area and contour of the seating surface.

* * * * *